United States Patent [19]
Ohnishi

[11] Patent Number: 5,006,512
[45] Date of Patent: Apr. 9, 1991

[54] THERAPEUTIC USAGES OF INHIBITORS FOR A POTASSIUM EFFLUX CHANNEL

[76] Inventor: Tsuyoshi Ohnishi, 502 King of Prussia Rd., Radnor, Pa. 19087

[21] Appl. No.: 289,072

[22] Filed: Dec. 22, 1988

Related U.S. Application Data

[63] Continuation-in-part of Ser. No. 104,199, Oct. 2, 1987, abandoned.

[51] Int. Cl.$^5$ ...................... A61K 37/02; A61K 35/58
[52] U.S. Cl. .......................................... 514/21; 514/2; 514/815; 424/542
[58] Field of Search ............................ 424/98; 435/69; 530/343, 858; 514/2, 21, 815

[56] References Cited

PUBLICATIONS

Sigma Chemical Company Catalog (1989), p. 1250.
Gelmers, Am. J. Cardiol. (1985), 55:144B–148B.
Ohnishi et al., Biol. Abstracts, vol. 82(13), 20391, 1986.
Miller et al., Nature, vol. 313 (Jan. 24, 1985), pp. 316–318.
Smith et al., J. Biol. Chem., vol. 261, No. 31 (Nov. 5, 1986), pp. 14607–14613.

Primary Examiner—Jacqueline Stone
Attorney, Agent, or Firm—Caesar, Rivise, Bernstein, Cohen & Pokotilow, Ltd.

[57] ABSTRACT

The invention provides novel therapeutic usages of inhibitors of a potassium channel of the cells. Since the increase of the intracellular calcium concentration is known to trigger various reactions which destroy the cells, the prevention of calcium entry by calcium channel blockers are known to be beneficial in protecting cell membranes in ischemic and traumatic injuries. However, the importance of potassium ions in cell injuries has not been well recognized. Using charybdotoxin (which is not a calcium channel blocker, but is a potassium channel blocker), the inventor found that this compound as well as related compounds have protecting effects in brain is chemia, liver ischemia and spinal cord injury at an extremely low concentration (0.05–0.14 mg/kg body weight). In in vitro experiments, these compounds inhibited the irreversible denaturation of sickle red cell membranes caused by sickling-unsickling stress at an extremely low concentration ($2 \times 10^{-8}$ M).

In an attempt to prepare a polypeptide molecule from charybdotoxin, the inventor digested charybdotoxin with an enzyme, fractionated by a size extrusion column chromatography, and obtained a polypeptide with the molecular weight of approximately 3,000. This new compound was named MR-117 for an identification purpose. It was demonstrated that MR-117 had protective effects on various organs and on sickle cells.

3 Claims, 6 Drawing Sheets

THERAPEUTIC USAGES OF INHIBITORS FOR A POTASSIUM EFFLUX CHANNEL

RELATED APPLICATION

This application is a continuation-in-part application based on prior application, which is Ser. No. 104,199 filed Oct. 2, 1987 entitled, "Pharmacologic Usages of Inhibitors for the Calcium-Activated Potassium Efflux" now abandoned. The entire disclosures of the aforesaid application are incorporated herein by reference.

BACKGROUNDS OF THE INVENTION

1. Field of the Invention

The present invention relates to new pharmacologic usages of inhibitors for a potassium efflux channel to prevent cell death caused by physical and chemical trauma, such as ischemia, hypoxia and contusion. These inhibitors can also protect sickle red blood cells from sickling-unsickling damages.

2. Background Art

Figure 1A:
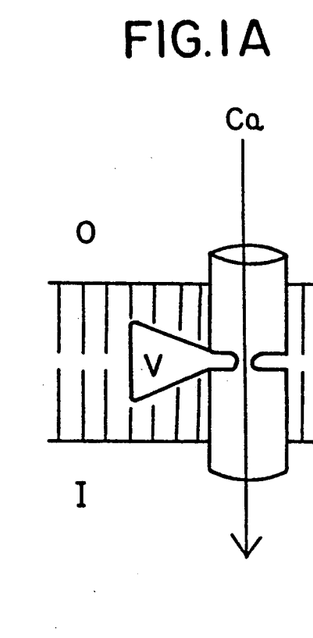
Figure 1B:
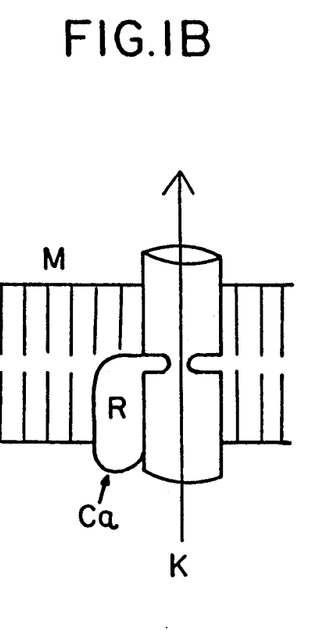
Figure 1C:
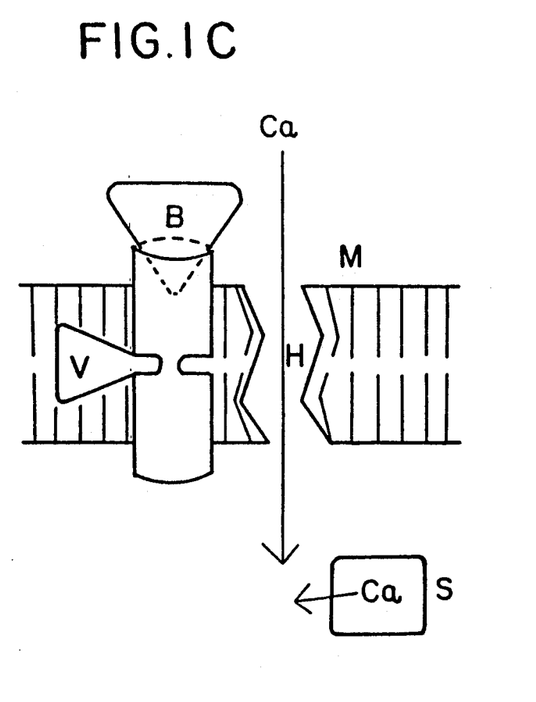

It has been established that most cells have both membrane potential-dependent calcium influx channels and potassium efflux channels (FIG. 1). The former channels are opened when the membrane is depolarized to cause calcium entry. This calcium entry can be blocked by calcium channel blockers. The latter channels are opened when the intracellular calcium concentration is increased to cause potassium ion efflux. The potassium efflux channels are different from the calcium entry channels, and were found by Gardos (Biochim. Biophys. Acta 30:653–654, 1958).

In ischemic or traumatic injury of the cells, the membrane is often depolarized as a result of injury. Therefore, the use of calcium channel blocker is known to be beneficial against these insults. However, when the cell membranes are damaged because of these insults, calcium ions may either enter the cells directly through the ruptured holes or released from the intracellular store (see FIG. 1). Since such movements of calcium ions can not be prevented by calcium channel blockers, the use of calcium channel blockers in cell injuries have had a limited success.

The present invention is based upon our study how to protect the cells when the intracellular calcium concentration increases as a result of cell injuries. So far, nobody has studied the importance of the potassium efflux channels. However, the inventor found that inhibitors of a potassium efflux channel have beneficial effects in protecting cells on the occasion of cell injuries. When an increase of cellular calcium ions is caused in organ cells or in red blood cells by ischemia, hypoxia or by physical-chemical damages, the cells lose potassium ions through a potassium efflux channel.

Such a loss causes unbalances both in cellular electrolytes and in water contents, and ultimately kills the cells. Through animal and in vitro experiments, the inventor found that compounds which can inhibit this potassium efflux have beneficial effects in preventing cell death in brain ischemia, spinal cord injury, liver ischemia, and in sickle red blood cells.

SUMMARY OF THE INVENTION

Charybdotoxin (abbreviated as MR-103 in this application for an identification purpose) is not a calcium channel blocker, but is a highly specific inhibitor of potassium efflux caused by an increase of intracellular calcium concentration. The inventor found that this compound can protect cells against ischemic and traumatic injuries. At a very low concentration, MR-103 protected the brain and liver of the rat from ischemic damages. MR-103 also protected the rat spinal cord from contusion injury. In in vitro experiments, MR-103 protected sickle red blood cells from sickling-unsickling-induced damage at an extremely low cocentration ($2 \times 10^{-8}$M).

MR-103 was decomposed by a protein digesting enzyme to form a polypeptide molecule with a molecular weight of approximately 3,000. This new compound was named MR-117 for identification purpose. It was demonstrated that MR-117 had beneficial, protective effects against cell injuries. Since a polypeptide of this size can be synthesized, this invention will lead to the use of a synthesized polypeptide for cell protection.

DETAILED DESCRIPTION OF THE INVENTION

Examples of this invention are set forth below. However, it is to be understood that these examples are given by way of illustration only and are not to be construed as limiting the invention either in spirit or in scope, as many modifications both in composition of reagents and methods could be possible to those skilled in the art.

DRUG PREPARATION METHODS

(a) Preparation of MR-103 from Scorpion Venom

The method of Smith et al. (J. Biol. Chem. 261:14607–14613, 1986) was used with a slight modification. In brief: A 200 mg sample of venom *L. quinquestriatus* was dissolved in 35 ml of buffer A (40 mM NaCl, 10 mM Na-borate, 10 mM $Na_2CO_3$, pH 9.0), and the undissolved mucoid material was removed by centrifugation at $5000 \times g$ for 10 minutes. The supernatant was saved and the pellet extracted twice in 10 ml of buffer A. The combined supernatant was loaded onto a 5-ml column of SP-Sephadex equilibrated with buffer A. The column was washed with 35 ml of buffer A, until the $A_{280}$ of the eluate fell to below 0.08. A linear gradient (80 ml total volume) of buffer A to buffer B (20 mM NaCl, 10 mM $Na_2CO_3$, 10 mM $Na_2HPO_4$, pH 12.0) was then applied to the column, and the protein concentration and pH of the eluent were followed. The peak of MR-103 activity was found to elute at pH 10.8–11.0.

Active fractions from the SP-Sephadex column were neutralized by addition of acetic acid, and were further fractionated by reverse-phase HPLC, using a 150A pore C8 column. Sample (about 200 ug protein) was applied to the column, which was then washed with 5 ml of buffer C (41 mM acetic acid, 9 mM ammonium-acetate, pH 3.9). A linear gradient (15 ml total volume) of buffer C to buffer D (50 mM acetic acid in 50% methanol) was run at 1 ml/min, and $A_{280}$ was monitored. The major peak of MR-103 was eluted at 25–30% methanol. Purified MR-103 was freeze-dried and stored at $-20°$ C.

(b) Preparation of Subfragment of MR-103

A solution containing 0.5 mg/ml of MR-103, 0.5 mg/ml of V-8 protease and 10 mM glycine buffer (pH 2.5) was incubated at 30° C. for 12 hours. V-8 protease is known as Catalogue No. P-2922 of Sigma Chemical Co. of St. Louis, Missouri. Then the solution was applied to a Sephadex G-25 column (20×900 mm) column. Then it was eluted by a 10 mM phosphate buffer (pH 6.5) at the velocity of 0.5 ml/min. The protein concentration of the eluent was monitored by recording the UV absorption at 280 nm. The third peak, which had a molecular weight of 3,000, was found to have beneficial effects both in ischemia and in sickle cell anemia. This compound seems to have a therapeutic value. Thus, this compound in named as MR-117 in this application for an identification purpose.

Toxicity test:

Acute toxicity ($LD_{50}$) was determined using mice, to which drugs were injected i.p. The $LD_{50}$ of MR-103 and MR-117 were 0.79 mg/kg and 0.92 mg/kg, respectively.

EXPERIMENTAL DESIGN AND RESULTS

Example 1

Effect of the Drug on Liver Ischemia

Figure 2:
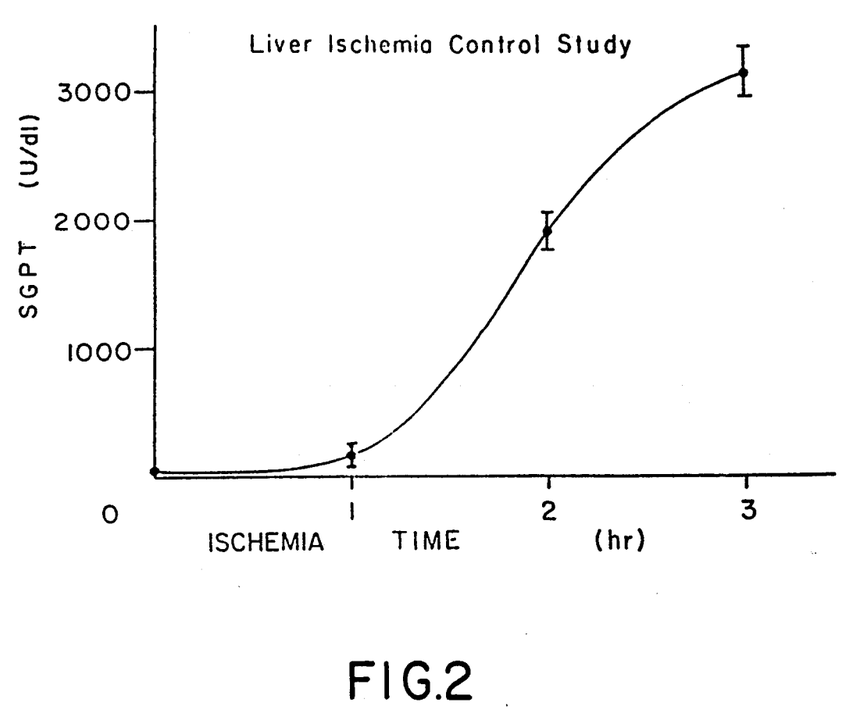
FIG. 2: Effect of global liver ischemia on the level of SGPT. Abscissa indicates the ischemia time. Blood samples were taken 24 hours after ischemia for SGPT assay.

Rats averaging between 150 to 175 grams were used. Under enflurane anesthesia, a microvascular clamp was placed to occlude the portal vein as well as the hepatic artery, which supplies blood to the left lateral and median lobes of the liver. The rats were subjected to ischemic conditions ranging from 1 to 3 hours, after which reperfusion of the liver was allowed by removing the clamp. Twenty four hous later, blood samples were drawn for the SGPT (serum glutamate-pyruvate transaminase) assay. As shown in FIG. 2, after 2 or 3 hours ischemia, the SGPT level steeply increased (to the levels of 2,000 to 3,000 U/dl) from the control level (which is about 100 U/dl). Using 2 hours of ischemia, we tested the effect of the drug. As shown in Table 1, MR-103 suppressed the increase of SGPT levels by about 60%.

TABLE 1

Protective effect of MR-103 against liver ischemia
SGPT values were measured 24 hours after 2 hours ischemia.

| Dose | SGPT (U/dl) |
| --- | --- |
| No drug | 1,927.1 |
| MR-103 (0.05 mg/kg) | 756.3 |

Example 2

Effects of Drugs on Brain Ischemia (a) Surgical procedures: Adults male Sprague-Dwaley rats weighing 250-300 g were used in these studies. Anesthesia was induced and maintained with halothane (1.0-2.5%) via closely fitted facial mask. Bilateral common carotid arteries (CCA) were exposed gently and the right CCA was ligated in two places by 4-0 silk suture. To expose the right middle cerebral artery (MCA), the temporal muscles were cut and retracted, then, a small temporal craniotomy (2=2 mm) was performed with a microdrill. Under a microscope, the dura matter was opened with a 26 guage needle, and the MCA was ligated by 10-0 suture with a square knot. Immediately, the left CCA was occluded by a microaneurysmal clip. After the operation, the animal was returned to the cage. One hour later, the left CCA clip was released under awake condition. The sham-operated control was produced in a similar procedure, except for the ligation and clipping of vessels. The operation was usually finished within 30 min.

(b) Water content and ionic analysis: After fixed time interval (1, 3, and 7 days), the animal was sacrificed and the excised cerebral hemispheres were placed in pre-weighed crucible and measured an wet weight (W.W) with a chemical balance (Mettler, AE 100). The samtle was then dried in a oven at 105° C. until it reached a constant weight, which was defined as a dry weight (D.W). The water content (% wet weight) was calculated by (W.W − D.W)/W.W.

Figure 3:
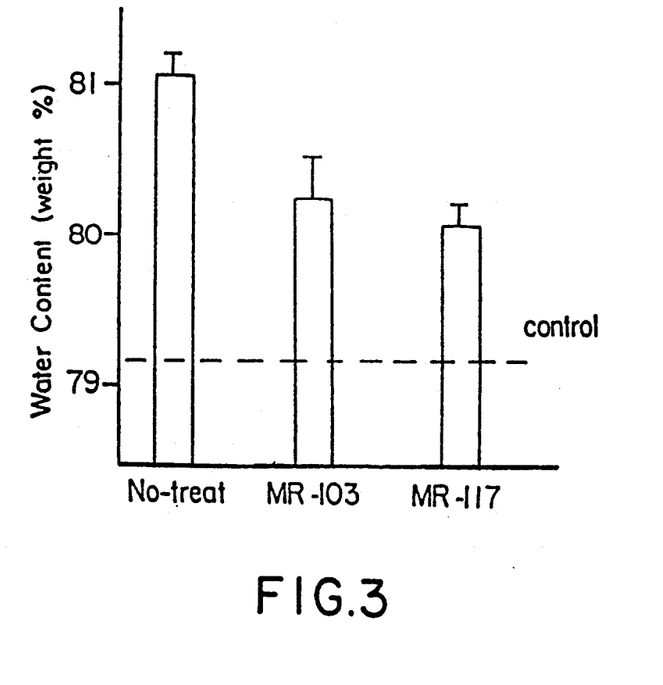
FIG. 3: Increase of the water content of the hemisphere of rat brain by 1 hour focal ischemia. The water content of the ischemia-exposed hemisphere increased from the control level (which is shown by the dashed line). Mr-103 and MR-117 (both 0.14 mg/kg i.v.) inhibited the increase of water content.

The water content of right hemisphere (ischemia side) was increased, showing that the brain edema was developed. If 0.14 mg/kg of either MR-103 or MR-117 was administered i.v. thirty minutes prior to ischemic insult, the increase of water content was much reduced as shown in FIG. 3.

(c) Motor performance test: The disturbance of motor function was evaluated by the total score obtained from inclined plate test, balance beam test and prehensile test. These motor performance tests were dsesigned to quantify the motor weakness in the global ischemia rats. We partially modified the original method to suit the rat focal ischemia model employed in this study, in which motor defeicts may be less severe than those in global ischemia (4-vessel occlusion, 20 min). Two trials were given to the animal, and the better score was chosen as the data. To lessen the factor of fatigue, the trial was carried out with a few minutes interval. In the inclined plate test, a 60×30 cm board patched with a thin rubber pad was used as a plate and was fixed at a designated angle (60°). The animal was placed at the highest position of the plate and the time which it could stay on the plate was measured untill 30 sec. In the balance beam test, a wooden rod, 70 cm long and 3.2 cm diameter, was positioned horizontally 60 cm above a thick sponge pad and the animal was left at the center of rod. The time spent on the rod was recorded untill 30 sec. In the prehensile test, a nylon rope, 70 cm long and 4 mm in diameter, was stretched horizontally 60 cm above a thick sponge pad and the forepaws of rat were placed on the rope and released. The time spent in hanging on the rope was measured untill 30 sec. The scoring method in these three tests was the same and defined as follows; 0:0 sec; 1:1-10 sec; 2:11-20 sec; 3:21-30 sec; 4: above 30 sec. Therefore, the total motor score ranged from 0 to 12 points.

Figure 4A:
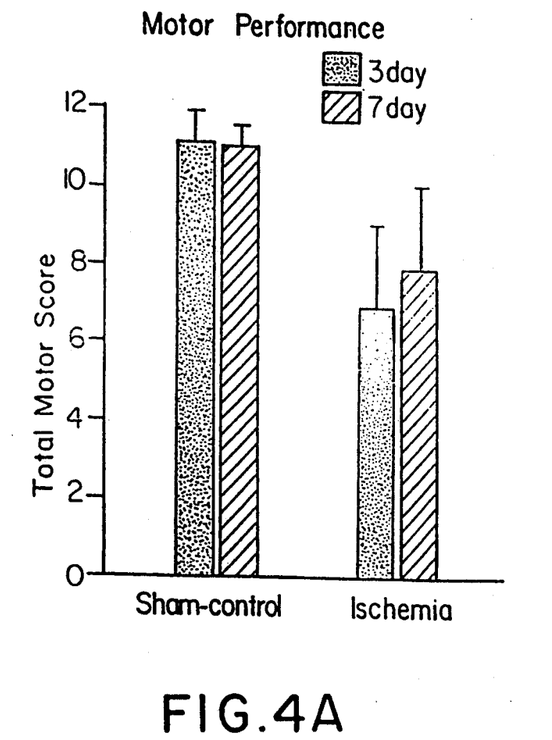
FIG. 4: Motor performance of rats exposed to 1 hour brain focal ischemia. (A) Effects of ischemia and (B) Beneficial effect of MR-103 on ischemia-exposed rats. Dotted columns: 3 days after ischemia. Hatched columns: 7 days after ischemia. Note that brain ischemia decreased the total motor score of the rat as shown in (A), but MR-103 reversed the decrease as shown in (B).
Figure 4B:
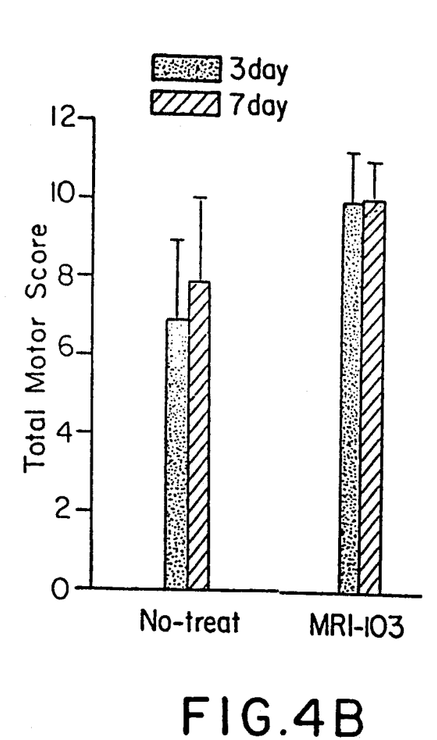

FIG. 4 shows the motor function as determined by these three tests (complete paralysis is indicated by the motor score 0, and normal condition as 12). By focal ischemia, the animal lost 3 days later about 50% of motor ability as indicated by the motor score of 7 in non-treated animals. In 7 days, animals recovered to approximately the score of 8. With 0.14 mg/kg MR-103 given before ischemia, the motor score obtained seven days after the operation was about 11 indicating that animals were almost completely recovered. MR-117 (0.14 mg/kg) also had a remarkable recovery effect (Table 2).

TABLE 2

Protective effect of MR-117 against the loss of motor performance caused by brain focal ischemia. Data was taken 3 days after ischemia.

| Condition | Motor Score |
| --- | --- |
| No drug | 6.93 ± 0.54 |
| MR-117 (0.14 mg/kg) | 9.50 ± 0.56 |
| Sham-control | 11.13 ± 0.28 |

(d) Passive avoidance test: The apparatus consists of an illuminated large compartment (40×40 cm) and a dark small compartment (10×10 cm). At the bottom of the small compartment, grids made of metal conductors were placed. Two compartments were connected through an opening (6×6 cm). The rat was placed on a fixed location in the large compartment and was allowed to explore the apparatus for 180 seconds.

The time spent in the small compartment was recorded with a stop watch. Then, when the rat was in the small compartment, the opening was closed with a transparent shutter and the rat received a weak electric shock for 30 sec (to a degree that the rat felt a slight pain). By this method, the rat had a experience of fear (learning) and passive avoidance reaction was established. The retention test was undertaken 24 hours after the learning experience in the same manner as the first exploratio process.

Figure 5A:
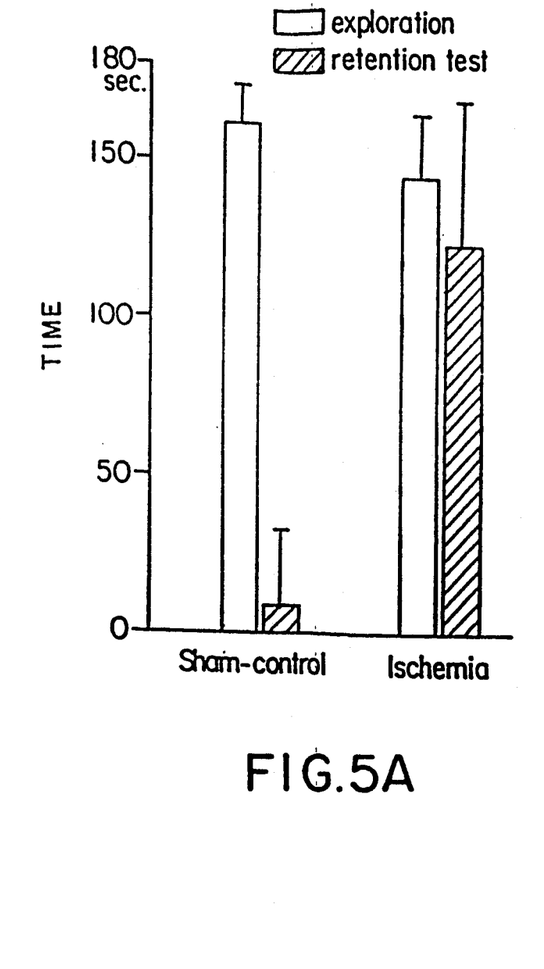
FIG. 5: Experiment of memory disturbance by the passive avoidance test. (A) Sham-control rats maintained memory so that they did not go back to the dark room after they learn about electric shock. However in ischemia rats, the retention time (time of going into the dark room after having learned the shock) was more than 120 seconds indicating that memory was disturbed. (B) by injecting MR-103 (0.14 mg/kg i.v.) half hour before ischemia, the retention time was remarkably decreased indicating that memory was retained.
Figure 5B:
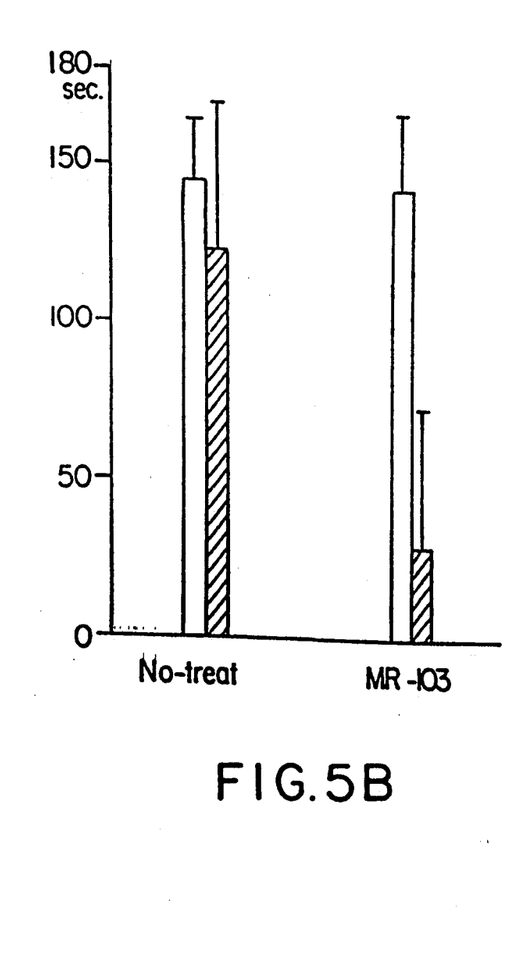

After receiving the electric shock, normal rats remembered the pain and never went back to the dark room again (the retension time was 0). However, in ischemia rats, memory was disturbed; they went back into the dark room. FIG. 5 shows that ischemic rats spent approximately 120 seconds in the dark room (as shown by shadowed column of retention time).

When the drugs were administered before the ischemia, animals maintained better memory as shown in FIG. 5. The retention time was signicantly decreased (to 40 to 50 seconds).

Example 3

Spinal Cord Injury

In spinal cord injury, the primary injury is accompanied by both an immediate loss of nerve action potential and a rapid ion movement. This is followed by secondary events which result in cell death in a matter of hours. We have found that drugs developed by the inventor are able to interrupt the chain of events that lead to cell death.

(a) Experimental procedure: A method developed by Wrathall's group (Wrathall et al. Exper. Neurology 88:108-122, 1985; Noble, L. J. and Wrathal, J. R. Exper. Neurology 95:530-533, 1987) was used. Animals were anesthetized with nembutal (50 mg/kg). Laminectomy was performed on T-11. Skin was tentatively closed and the animal was recovered from anesthesia. Several hours later, the animal was anesthesized with 1.5% halothane (air as a carrier). T-11 was again exposed and an impounder (made of plastic with a tip diameter of 2.4 mm) was placed on the exposed dura. Then, a 10 gram weight was dropped from the height of 5 cm onto the impounder. The impounder remained on the surface of the spinal cord for a few seconds, after which it was removed. The skin was sutured. The animal was returned to the cage after regaining consciousness.

Figure 6:
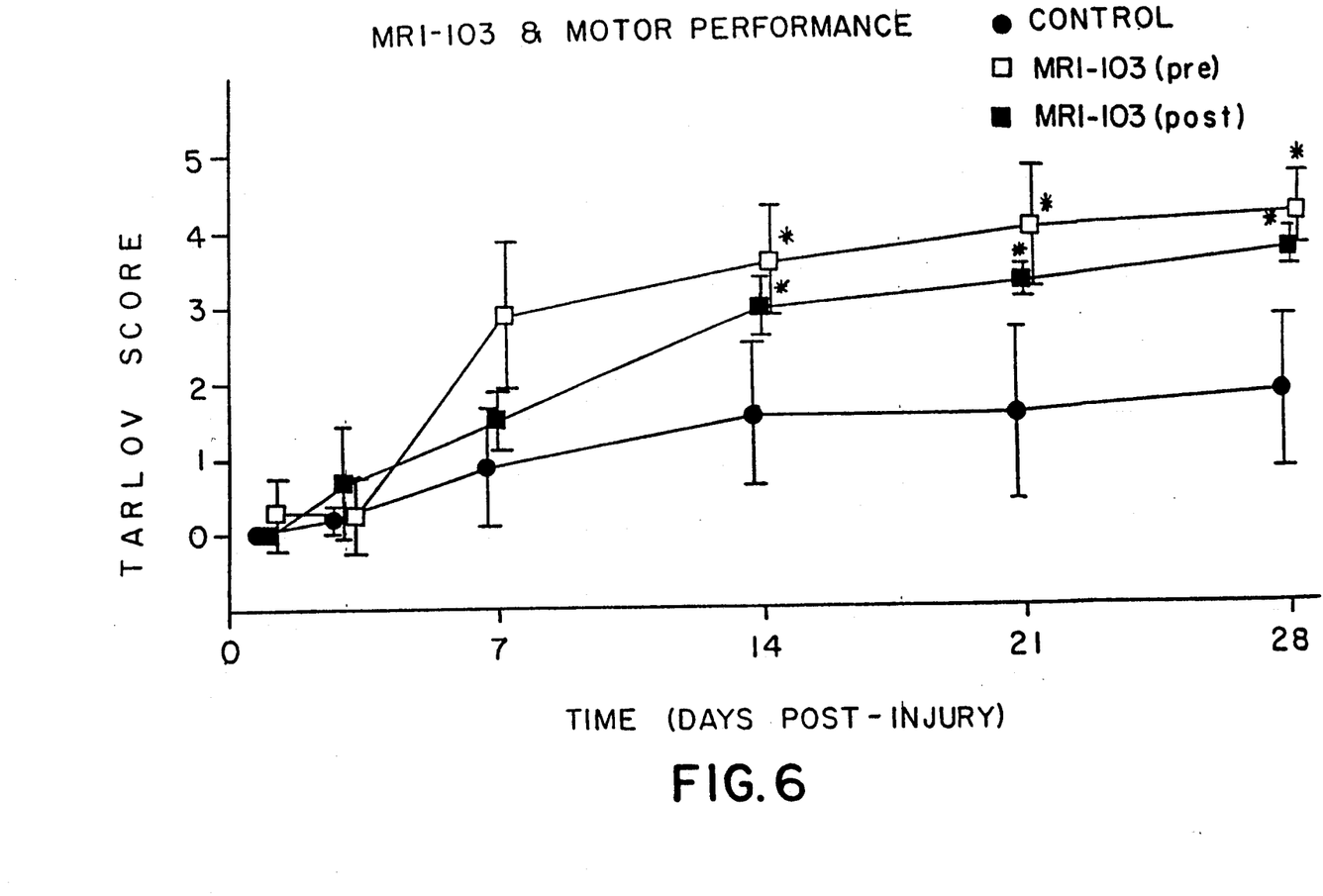
FIG. 6: Motor performance as measured by the Tarlov Score with rats received a dynamic contusion injury on the spinal cord. In control (no drug) experiment, rats were still paralyzed after 4 weeks, while pre-administration (30 minutes before injury) of MR-103 (0.15 mg/kg) improved remarkably the motor performance. Post-administration (3 minutes after the contusion) was slightly less effective than pre-administration.

(b) Assessment of motor recovery: After contusion, animals were observed for four weeks during which time the recovery was quantified by rating the hindlimb walking ability according to the method originally used by Tarlov (Tarlov, I. M. Arch. Neurol. psychiatry 71:588-597, 1954) and modified by Wrathall et al. (Exper. Neurology 88:108-127, 1985). This is basically a scoring system for hind limb mobility ranging from 0-5. Zero indicates complete paralysis, while a score of 5 indicates full recovery. Measurements were taken from a group of rats receiving no treatment (control) and a group receiving a drug treatment either 30 minutes before injury (pre-treatment) or 30 minutes after injury (post-treatment). The drug was administered i.v. (0.14 mg/kg body weight). As shown in FIG. 6, MR-103 improved the recovery. The pre-treatment was more effective than the post-treatment.

Example 4

Sickle Cell Anemia

The inventor previously developed a method to produce irreversibly sickled cells (ISC, which have irreversibly denatured membranes) by exposing sickle red blood cells to a repeated sickling-unsickling cycling in vitro. He used this system to determine the efficacy of a drug in protecting cell membranes (Ohnishi, Br. J. Haematol. 55:665-671, 1983). When sickle cells were exposed to a sickling-unsickling cycling for one hour, about a half of cells was denatured as revealed by the formation of heavy, dehydrated cells in density gradient centrifugation. These heavy cells were collected, the amount measured, and the percentage of production calculated (Table 3). As shown in the Table, MR-103 inhibited the formation of irreversibly denatured cells at an extremely low concentration. Even at 20 nM, it inhibited the production of denatured cell almost 50%. At 60 nM, the production was almost completely inhibited. The subfragment comound MR-117 was also found to have a remarkable effect (Table 4). At a concentration of 60 nM, it inhibited the formation of denatured cells by more than 50%.

TABLE 3

Protective effect of MR-103 against the formation of irreversibly sickled cells caused by sickling-unsickling cycling (numbers incicate the percentages)

| | drug during cycling | | | | no cycling |
|---|---|---|---|---|---|
| | 0 | 20 | 60 | 120 nM | 0 nM |
| Reversibly sickling cells | 10.3 | 47.2 | 95.6 | 100 | 100 |
| Irreversibly sickling cells | 89.7 | 52.8 | 4.4 | 0 | 0 |

TABLE 4

Protective effect of MR-117 against the formation of irreversibly sickled cells caused by sickling-unsickling cycling (numbers incicate the percentages)

| | drug during cycling | | | | no cycling |
|---|---|---|---|---|---|
| | 0 | 60 | 100 | 200 nM | 0 nM |
| Reversibly sickling cells | 64.1 | 85.2 | 89.7 | 100 | 100 |
| Irreveribly sickling cells | 35.9 | 14.8 | 10.3 | 0 | 0 |

FIGURE LEGENDS

FIG. 1: Schematic illustrations of a cell membrane (indicated by M) and channels (illustrated by cylinders). The outside and inside of the membrane are indicated by (O) and (I), respectively. (A) A membrane potential-dependent calcium entry channel. V represents the potential sensor which can open the channel to cause the entry of calcium ions (shown by Ca). (B) a potassium efflux channel which is opened by an increase of the intracellular calcium concentration. R is a calcium receptor which detects an increase of the intracellular calcium concentration to open the channel for potassium efflux (shown by K). (C) When the cell membrane is ruptured by ischemia, hypoxia or trauma, the intracellular calcium concentration could increase by either (i) entry of external calcium ions through the ruptured hole (indicated by H) or (ii) release of calcium ions from intracellular calcium stores (shown by S). Thus, the efficacy of calcium channel blockers (shown by B) to protect the cell from the increase of intracellular calcium concentration is limited.

What is claimed is:

1. A method of preventing cell death of the brain, the spinal cord and the liver against ischemia, hypoxia or injury in a human or animal by administering an effective dosage of charybdotoxin either pre-injury or post-injury, in the amount of at least 0.2 mg/kg body weight/day, subcutaneously at least 0.15 mg/kg/day or i.v. at least 0.1 mg/kg/day.

2. A method of preventing cell death of the brain, the spinal cord and the liver against ischemia, hypoxia or injury by administering MR-117 via routes and doses described in claim 1.

3. A method of protecting sickle red cell membranes from sickling-unsickling damages by administering MR-117, polypeptide molecules, via routes and doses described in claim 1.

* * * * *